United States Patent
Kikuchi

(10) Patent No.: US 10,246,566 B2
(45) Date of Patent: Apr. 2, 2019

(54) POLYETHYLENE POLYMER POWDER AND METHOD OF PRODUCING SAME

(71) Applicant: ASAHI KASEI KABUSHIKI KAISHA, Chiyoda-ku, Tokyo (JP)

(72) Inventor: Akitomo Kikuchi, Tokyo (JP)

(73) Assignee: ASAHI KASEI KABUSHIKI KAISHA, Chiyoda-ku, Tokyo (JP)

(*) Notice: Subject to any disclaimer, the term of this patent is extended or adjusted under 35 U.S.C. 154(b) by 0 days.

(21) Appl. No.: 15/924,682

(22) Filed: Mar. 19, 2018

(65) Prior Publication Data

US 2018/0273708 A1 Sep. 27, 2018

(30) Foreign Application Priority Data

Mar. 21, 2017 (JP) .................. 2017-054988

(51) Int. Cl.
| | |
|---|---|
| *C08J 3/28* | (2006.01) |
| *C08F 10/02* | (2006.01) |
| *A61L 27/16* | (2006.01) |
| *A61F 2/34* | (2006.01) |
| *A61F 2/30* | (2006.01) |

(52) U.S. Cl.
CPC ................. *C08J 3/28* (2013.01); *A61F 2/34* (2013.01); *A61L 27/16* (2013.01); *C08F 10/02* (2013.01); *A61F 2002/30065* (2013.01); *A61L 2430/24* (2013.01); *C08F 2810/20* (2013.01); *C08J 2323/06* (2013.01)

(58) Field of Classification Search
CPC .......... C08J 3/28; C08J 2323/06; C08F 10/02; C08F 2810/20; A61L 27/16; A61L 2430/14; A61F 2/34; A61F 2002/30065
See application file for complete search history.

(56) References Cited

U.S. PATENT DOCUMENTS

| | | |
|---|---|---|
| 2009/0326170 A1 | 12/2009 | Dewachter |
| 2016/0152744 A1 | 6/2016 | Inatomi et al. |
| 2017/0125763 A1* | 5/2017 | Inatomi ................ B01D 53/228 |

FOREIGN PATENT DOCUMENTS

| | | |
|---|---|---|
| JP | H11255823 A | 9/1999 |
| JP | 2005313391 A | 11/2005 |
| JP | 2009532550 A | 9/2009 |
| JP | 2015504935 A | 2/2015 |
| KR | 1020010041816 A | 5/2001 |
| WO | 9946302 A1 | 9/1999 |
| WO | 2013093540 A1 | 6/2013 |
| WO | 2015005287 A1 | 1/2015 |

OTHER PUBLICATIONS

May 8, 2018, Decision to Grant a Patent issued by the Japan Patent Office in the corresponding Japanese Patent Application No. 2017-054988.

* cited by examiner

*Primary Examiner* — Robert D. Harlan
(74) *Attorney, Agent, or Firm* — Kenja IP Law PC

(57) ABSTRACT

Provided are a polyethylene polymer powder and method of producing the same that can improve molding efficiency while maintaining high levels of molded product strength and wear resistance. The polyethylene polymer powder comprises an ethylene homopolymer or copolymer and has an intrinsic viscosity IV of at least 12 dL/g and not more than 35 dL/g, a melting peak full width at half maximum of at least 2° C. and not more than 7° C., a span (laser particle size distribution measurement) of at least 0.9 and not more than 2, and an α-olefin content of 0 mol % to not more than 1.50 mol %. The method of producing this polyethylene polymer powder includes polymerizing ethylene or ethylene and an α-olefin by slurry polymerization using a loop reactor. In the polymerizing, supply of a solvent and ethylene or supply of a solvent, ethylene, and an α-olefin is performed by a plurality of supply lines.

10 Claims, No Drawings

POLYETHYLENE POLYMER POWDER AND METHOD OF PRODUCING SAME

TECHNICAL FIELD

This disclosure relates to a polyethylene polymer powder and a method of producing this polyethylene polymer powder.

BACKGROUND

Polyethylene having an ultra-high molecular weight exceeding several hundred thousand has dramatically improved impact resistance, self-lubrication, wear resistance, weather resistance, chemical resistance, and dimensional stability, and exhibits high physical properties on a par with those of engineering plastics. Consequently, the application thereof in lining materials, line parts in the food industry, machine parts, prosthetic joints, sports equipment, fibers, filters in which porous sinter formed products are used, separators for secondary batteries such as lead-acid batteries and lithium ion batteries in which microporous membranes are used, and so forth has been attempted by various shaping methods.

CITATION LIST

Patent Literature

PTL 1: WO 2015-005287 A1

SUMMARY

Ultra-high molecular weight polyethylene is normally obtained as a powder after polymerization. The ultra-high molecular weight of this polyethylene means that a specialized shaping method may be adopted for shaping of the polyethylene powder. Specific examples of methods by which ultra-high molecular weight polyethylene can be shaped include a method in which the powder obtained through polymerization is directly sintered, a method in which compression molding is performed, an extrusion molding method using a ram extruder that performs extrusion molding while performing intermittent compression, and a method in which extrusion molding is carried out with the powder in a dispersed state in a solvent or the like and the solvent is subsequently removed.

With regards to ultra-high molecular weight polyethylene, there is demand for sufficient improvement of molding efficiency from a viewpoint of further production cost reduction, for example. However, when molding cycles have been quickened with the aim of improving molding efficiency, there have been cases in which it has not been possible to obtain desired physical properties such as molded product strength and wear resistance due to ultra-high molecular weight polyethylene being a powder of particles in various forms. In particular, although ultra-high molecular weight polyethylene has excellent physical properties as described above, molded products thereof have not been able to adequately meet the high levels of physical properties demanded for adoption in high-performance and high-quality applications in which these molded products are to be used.

Moreover, although various studies have been carried out in relation to, for example, techniques for increasing the strength of obtained molded products in molding methods such as described above (for example, PTL 1), a technique that both improves molding efficiency and maintains high levels of strength and wear resistance has not yet been disclosed.

Accordingly, this disclosure is made in light of the problems set forth above and aims to provide a polyethylene polymer powder and a method of producing the same that can improve molding efficiency while maintaining high levels of molded product strength and wear resistance.

As a result of diligent research, the inventor discovered that the problems set forth above can be solved through a specific polyethylene polymer powder and completed the present disclosure based on this discovery.

Specifically, this disclosure provides the following.

[1] A polyethylene polymer powder comprising an ethylene homopolymer or a copolymer of ethylene and an α-olefin having a carbon number of at least 3 and not more than 8, wherein the polyethylene polymer powder has an intrinsic viscosity IV of at least 12 dL/g and not more than 35 dL/g as measured at 135° C. in decalin solvent, the polyethylene polymer powder has a melting peak full width at half maximum of at least 2° C. and not more than 7° C. as measured by differential scanning calorimetry at a heating rate of 10° C./min, the polyethylene polymer powder has a span of at least 0.9 and not more than 2 as determined by laser particle size distribution measurement in methanol, and the polyethylene polymer powder has an α-olefin content of 0 mol % to not more than 1.50 mol % as measured by $^{13}$C-NMR.

[2] The polyethylene polymer powder according to the foregoing [1], wherein the polyethylene polymer powder has a heat of fusion ΔH1 of at least 100 J/g and not more than 200 J/g as measured by differential scanning calorimetry at a heating rate of 10° C./min, and a temperature at which 5% heat of fusion of the heat of fusion ΔH1 is reached is at least 90° C. and not higher than 120° C.

[3] The polyethylene polymer powder according to the foregoing [1] or [2] for a compression molded product.

[4] The polyethylene polymer powder according to the foregoing [1] or [2] for a prosthetic joint.

[5] A prosthetic joint comprising a crosslinked molded product obtained through γ-ray irradiation of a molded product of the polyethylene polymer powder according to the foregoing [1] or [2].

[6] A method of producing the polyethylene polymer powder according to the foregoing [1] or [2], comprising:

polymerizing ethylene or ethylene and an α-olefin by slurry polymerization using a loop reactor, wherein in the polymerizing, supply of a solvent and ethylene or supply of a solvent, ethylene, and an α-olefin is performed by a plurality of supply lines.

According to this disclosure, it is possible to provide a polyethylene polymer powder that can improve molding efficiency while maintaining high levels of molded product strength and wear resistance.

DETAILED DESCRIPTION (Polyethylene Polymer Powder)

A polyethylene polymer powder according to a present embodiment comprises an ethylene homopolymer or a copolymer of ethylene and an α-olefin having a carbon number of at least 3 and not more than 8. The polyethylene polymer powder has an intrinsic viscosity IV of at least 12 dL/g and not more than 35 dL/g as measured at 135° C. in decalin solvent, a span of at least 0.9 and not more than 2 as determined by laser particle size distribution measurement in methanol, and an α-olefin content of 0 mol % to not more than 1.50 mol % as measured by $^{13}$C-NMR.

Through the configuration set forth above, molding efficiency can be improved while maintaining high levels of molded product strength and wear resistance.

Specifically, as a result of the polyethylene polymer powder according to the present embodiment having a span in the prescribed range, particles of various particle diameters are included in the powder, which means that gaps between the particles can be reduced when the powder is loaded into a molding device (for example, a mold) for molding.

Moreover, even when particles of a powder are effectively loaded, it is essential that there is suitable heat conduction to each particle in the powder (structure) during molding such as to melt the particles. In the present embodiment, fine particles are present in the powder to an appropriate degree as a result of the powder having a span in the prescribed range. These fine particles can act as a trigger for melting in the powder (structure) in an initial stage of molding and can efficiently melt into the powder (structure). Moreover, as a result of the polyethylene polymer powder having an intrinsic viscosity IV in the prescribed range, the molecular weight of the polymer can be set in an appropriate range. Consequently, it is possible to avoid a situation in which portions that do not readily melt due to having an excessively high molecular weight arise, and thus favorable melting of the powder (structure) can be achieved. Furthermore, non-uniformities tend to arise in melting if a powder has a melting peak with an excessively wide full width at half maximum. However, since this full width at half maximum is not excessively wide in the present embodiment, non-uniformities tend not to arise in melting, and uniform melting can be achieved.

Therefore, through the polyethylene polymer powder according to the present embodiment, heat for molding is uniformly and efficiently conducted into an effectively loaded powder (structure), which enables efficient melting of the entire powder (structure) without excess heating in molding (even when the heating temperature is lowered), for example, and thus can improve molding efficiency.

On the other hand, as a result of the powder being densely loaded and as a result of melting of particles and fusing among particles occurring uniformly, a molded product can be provided with a strong structure, which enables maintenance of high levels of strength and wear resistance of the molded product.

Therefore, the polyethylene polymer powder according to the present embodiment enables improvement of molding efficiency while maintaining high levels of molded product strength and wear resistance.

The various requirements set forth above are described in detail below.

The polyethylene polymer powder contains an ethylene homopolymer or a copolymer of ethylene and an α-olefin having a carbon number of at least 3 and not more than 8 (hereinafter, also referred to simply as a "comonomer"). Examples of comonomers that can be used in the present embodiment include, but are not specifically limited to, α-olefins represented by the following formula.

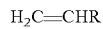

$H_2C=CHR$ (In the formula, R represents a linear or branched alkyl group having a carbon number of 1 to 6.)

Specific examples of comonomers that can be used include, but are not specifically limited to, propylene, 1-butene, 1-pentene, 1-hexene, 1-octene, and 4-methyl-1-pentene. Of these comonomers, propylene and 1-butene are suitable in terms of cost and ease of handling. The use of an α-olefin having a carbon number of 8 or less tends to result in excellent fusing of the polyethylene polymer powder and improved molding properties.

The intrinsic viscosity IV of the polyethylene polymer powder as measured at 135° C. in decalin solvent is at least 12 dL/g and not more than 35 dL/g, preferably at least 13 dL/g and not more than 34 dL/g, and more preferably at least 14 dL/g and not more than 33 dL/g. As a result of the intrinsic viscosity IV being 12 dL/g or more, strength and wear resistance of the polyethylene polymer itself can be improved, and as a result of the intrinsic viscosity IV being 35 dL/g or less, it is possible to avoid a situation in which portions that are difficult to melt arise in molding and maintain molding properties.

Examples of methods by which the intrinsic viscosity IV measured at 135° C. can be controlled to be at least 12 dL/g and not more than 35 dL/g in the present embodiment include, but are not specifically limited to, a method of altering the polymerization temperature of a reactor in polymerization. In general, molecular weight tends to become lower when a higher polymerization temperature is adopted and tends to become higher when a lower polymerization temperature is adopted. Another example of a method by which the intrinsic viscosity IV can be controlled to within any of the ranges set forth above is a method in which a chain transfer agent such as hydrogen, organoaluminum, or organozinc is added in polymerization of ethylene and the like. The addition of a chain transfer agent tends to lower the resultant molecular weight even for the same polymerization temperature. The intrinsic viscosity IV can be measured by a method described in the subsequent EXAMPLES section.

The melting peak full width at half maximum of the polyethylene polymer powder as measured by differential scanning calorimetry at a heating rate of 10° C./min is at least 2° C. and not more than 7° C., preferably at least 3° C. and not more than 6.5° C., and more preferably at least 3.5° C. and not more than 6° C. If the melting peak full width at half maximum is too small, the entire powder rapidly melts, which may lead to the presence of excess residual air or the like in a molded product. A full width at half maximum of 2° C. or more prevents excess residual air or the like in a molded product and tends to inhibit post-molding heat shrinkage caused by residual air or the like. Moreover, a full width at half maximum of 7° C. or less tends to facilitate control of melting of the powder and facilitate uniform melting.

Examples of methods by which the melting peak full width at half maximum can be controlled to be at least 2° C. and not more than 7° C. in the present embodiment include, but are not specifically limited to, a method in which feeding inlets for raw materials such as ethylene and an α-olefin, and a solvent such as hexane are split into two or more locations each and a method in which a metallocene catalyst is used. Since the melting peak full width at half maximum is an indicator that expresses the uniformity of melting behavior, it is anticipated that the melting peak full width at half maximum will be reduced by resolving temperature non-uniformity in the polymerization system such that the polymerization reaction proceeds uniformly. The melting peak full width at half maximum can be measured by a method described in the subsequent EXAMPLES section.

The span of the polyethylene polymer powder as determined by laser particle size distribution measurement in methanol is at least 0.9 and not more than 2.0, preferably at least 0.95 and not more than 1.80, and more preferably at least 1.0 and not more than 1.6. The span is an indicator that expresses the uniformity of a particle size distribution, and a larger span indicates a wider particle size distribution. A span of 0.9 or more tends to facilitate effective loading of the polyethylene polymer powder into a mold in molding of the powder, whereas a span of 2.0 or less restricts the presence of particles having an excessively large or small particle diameter and can facilitate uniform melting.

Examples of methods by which the span can be controlled to be at least 0.9 and not more than 2.0 in the present embodiment include, but are not specifically limited to, a method of using a continuous-type loop reactor in polymerization and also lengthening the residence time, a method of increasing the amount of α-olefin that is supplied in a case in which an α-olefin is used in polymerization, and a method of using a catalyst having a wide particle size distribution. It is thought that the use of a loop reactor increases the span because polymer particles are abraded during growth when the particles are circulated in the reactor, leading to the formation of fine powder. The span can be measured by a method described in the subsequent EXAMPLES section.

The α-olefin content of the polyethylene polymer powder as measured by $^{13}$C-NMR is 0 mol % to not more than 1.5 mol %, preferably at least 0.02 mol % and not more than 1.2 mol %, and more preferably at least 0.05 mol % and not more than 0.8 mol %.

Note that in a case in which the α-olefin content of the polyethylene polymer powder is 0 mol %, this indicates that the polyethylene polymer powder contains an ethylene homopolymer and does not contain a copolymer of ethylene and an α-olefin monomer having a carbon number of at least 3 and not more than 8 (hereinafter, also referred to simply as a "comonomer").

Examples of methods by which the α-olefin content may be controlled to be 0 mol % to not more than 1.5 mol % in the present embodiment include, but are not specifically limited to, a method of using a supported metallocene catalyst having high copolymerization performance and a method of adjusting the amount of an α-olefin that is fed to a polymerization vessel. The α-olefin content can be measured by a method described in the subsequent EXAMPLES section.

The heat of fusion ΔH1 of the polyethylene polymer powder as measured by differential scanning calorimetry at a heating rate of 10° C./min is preferably at least 100 J/g and not more than 200 J/g, more preferably at least 110 J/g and not more than 195 J/g, and even more preferably at least 120 J/g and not more than 190 J/g. When the heat of fusion ΔH1 is 100 J/g or more, the suitable temperature range in molding can be widened (i.e., molding properties can be improved), and when the heat of fusion ΔH1 is 200 J/g or less, the polyethylene polymer powder melts more easily and the molding time can be shortened, which enables improvement of molding efficiency. Examples of methods by which the heat of fusion ΔH1 may be controlled to be at least 100 J/g and not more than 200 J/g in the present embodiment include, but are not specifically limited to, a method of altering the type and copolymerization ratio of the α-olefin having a carbon number of at least 3 and not more than 8, a method of lowering the drying temperature in a dryer, a method of shortening the residence time in a dryer, and a method of increasing the amount of supported metallocene in preparation of a supported metallocene catalyst and carrying out the supporting at a lower temperature. The heat of fusion ΔH1 can be measured by a method described in the subsequent EXAMPLES section.

The temperature T5% at which 5% heat of fusion of the heat of fusion ΔH1 of the polyethylene polymer powder is reached as measured by differential scanning calorimetry at a heating rate of 10° C./min is preferably at least 90° C. and not higher than 120° C., and more preferably at least 95° C. and not higher than 110° C. When the temperature T5% at which 5% heat of fusion of the heat of fusion ΔH1 is reached is 90° C. or higher, the suitable temperature range in molding can be widened (i.e., molding properties can be improved), and when the temperature T5% is 120° C. or lower, the polyethylene polymer powder melts more easily and the molding time can be shortened, which enables improvement of molding efficiency.

Examples of methods by which the temperature T5% at which 5% heat of fusion of the heat of fusion ΔH1 is reached may be controlled to be at least 90° C. and not higher than 120° C. in the present embodiment include, but are not specifically limited to, a method of altering the type and copolymerization ratio of α-olefin in a case in which an α-olefin having a carbon number of at least 3 and not more than 8 is used in polymerization, a method of lowering the drying temperature in a dryer, a method of shortening the residence time in a dryer, and a method of increasing the amount of supported metallocene in preparation of a supported metallocene catalyst and carrying out the supporting at a lower temperature. The temperature T5% at which 5% heat of fusion of the heat of fusion ΔH1 is reached can be measured by a method described in the subsequent EXAMPLES section.

The average particle diameter D50 of the polyethylene polymer powder is preferably at least 50 μm and not more than 250 μm, more preferably at least 60 μm and not more than 220 μm, and even more preferably at least 70 μm and not more than 200 μm. An average particle diameter D50 of 50 μm or more can inhibit electrostatic adhesion and thereby improve handling properties, whereas an average particle diameter D50 of 250 μm or less can facilitate more uniform melting.

Examples of methods by which the average particle diameter D50 can be controlled to be at least 50 μm and not more than 250 μm in the present embodiment include, but are not specifically limited to, a method of using a continuous-type loop reactor in polymerization and also lengthening the residence time such as to improve activity and grow polymer particles, and a method of using a catalyst having a large average particle diameter. The average particle diameter D50 can be measured by a method described in the subsequent EXAMPLES section.

The polyethylene polymer powder according to the present embodiment may contain commonly known additives such as antioxidants (for example, phenolic, phosphoric, and sulfuric antioxidants), lubricants (for example, calcium stearate), antistatic agents, light stabilizers, and ultraviolet absorbers to the extent that the objectives of the present embodiment are not impeded.

As a result of the polyethylene polymer powder according to the present embodiment having a span, an intrinsic viscosity IV, and a melting peak full width at half maximum that are within prescribed ranges as described above, the powder can be densely loaded into a molding machine and can be uniformly melted. This enables improvement of the surface smoothness of a molded product obtained through molding of the powder and can provide a homogenized structure near the surface of the molded product.

Moreover, the configurational requirements relating to the polyethylene polymer powder described above can also be adopted with respect to a polyethylene polymer powder for obtaining a molded product, and through adoption thereof, surface smoothness of the molded product can be improved, and a sufficiently homogenized structure can be provided near the surface of the molded product.

The polyethylene polymer powder set forth above can be suitably used for a prosthetic joint, for example, but is not specifically limited to this use.

Specifically, in a prosthetic joint, a joint may, for example, be formed from a prosthetic bone head made from a metal or ceramic and a prosthetic acetabulum (socket) made from ultra-high molecular weight polyethylene having excellent wear resistance. However, when a prosthetic acetabulum made from ultra-high molecular weight polyethylene is subjected to long-term use in vivo, deformation and wear of the prosthetic acetabulum may occur. This wear is thought to be caused by reduction in molecular weight that occurs due to molecular chain scission at the surface of the ultra-high molecular weight polyethylene when crosslinking treatment is performed to improve creep deformation resistance. The crosslinking treatment is typically performed through recombination of radicals generated through irradiation of the molded product with γ-rays, and thus competes with molecular weight reduction due to molecular chain scission. Note that γ-ray irradiation also serves as sterilization treatment of the molded product in addition to crosslinking treatment and is, therefore, an essential process in a situation in which ultra-high molecular weight polyethylene is to be used in a prosthetic joint.

As one example of a conventional technique (JP 2984203 B), a technique has been disclosed in which ultra-high molecular weight polyethylene is irradiated with a large dose of γ-rays (500 kGy to 1,000 kGy in terms of absorbed heat rays), the ultra-high molecular weight polyethylene is then heat treated at 80° C. to 200° C. for approximately 30 minutes to 12 hours, and subsequently machining is performed to obtain a desired molded, and the material surface of ultra-high molecular weight polyethylene that has degraded due to γ-ray irradiation is removed by machining, which improves wear resistance. However, the conventional technique described above suffers from the following problems. Specifically, it is necessary to carry out machining to shape the ultra-high molecular weight polyethylene into a desired shape after the ultra-high molecular weight polyethylene had been crosslinked through γ-ray irradiation, and machining cannot be easily performed in this situation because there are locations at which the molecular weight has been further raised through the crosslinking. Moreover, it is necessary to use specialized equipment for the machining technique and the environment during machining because sterilization treatment has been performed through the γ-ray irradiation.

Therefore, with respect to polyethylene polymer powders, there is demand for the provision of a powder that has little surface degradation due to γ-ray irradiation and can be used for a prosthetic joint.

As a result of the polyethylene polymer powder according to the present embodiment having a span, an intrinsic viscosity IV, and a melting peak full width at half maximum that are within prescribed ranges as described above, the powder can improve surface smoothness of a molded product and can provide a homogenized structure near the surface of the molded product. Note that in a case in which the surface of the molded product is not smooth and the structure near the surface of the molded product is not homogeneous, non-uniformities may arise upon irradiation with γ-rays and thus portions that degrade more easily may be formed. However, since the molded product according to the present embodiment has good surface smoothness and the structure near the surface of this molded product has good homogeneity, degradation does not readily occur even upon irradiation with γ-rays. Moreover, as a result of the polymer of the polyethylene polymer powder having a high molecular weight, crosslinking tends to occur more readily than molecular weight reduction by molecular chain scission upon irradiation with γ-rays. This enables sufficient reduction of degradation after irradiation with γ-rays and can thereby improve wear resistance.

Accordingly, when the polyethylene polymer powder is used, surface degradation due to γ-ray irradiation is sufficiently small and thus wear resistance after irradiation with γ-rays can be improved.

A prosthetic joint that includes a crosslinked molded product (for example, a prosthetic acetabulum) obtained through γ-ray irradiation of a molded product of the polyethylene polymer powder according to the present embodiment can effectively reduce deformation and wear of the crosslinked molded product resulting from long-term use in vivo.

Note that although the intrinsic viscosity IV of the presently disclosed polyethylene polymer powder as measured at 135° C. in decalin solvent is set as at least 12 dL/g and not more than 35 dL/g, the intrinsic viscosity IV in the case of a polyethylene polymer powder for a prosthetic joint may be set as at least 12 dL/g and not more than 25 dL/g because the powder may be irradiated with γ-rays and crosslinked in use in a molded product as described above.

(Method of Producing Polyethylene Polymer Powder)

A method of producing a polyethylene polymer powder according to the present embodiment includes a polymerization step of obtaining the above-described polyethylene polymer powder through homopolymerization of ethylene or copolymerization of ethylene and an α-olefin having a carbon number of at least 3 and not more than 8 using a catalyst. The catalyst is preferably a supported metallocene catalyst such as described below.

<Supported Metallocene Catalyst>

The supported metallocene catalyst according to the present embodiment may be prepared using at least (A) an inorganic support material (hereinafter, also referred to as "component (A)" or "(A)"), (B) an organoaluminum compound (hereinafter, also referred to as "component (B)" or "(B)"), (C) a transition metal compound having a cyclic η-bonding anionic ligand (hereinafter, also referred to as "component (C)" or "(C)"), and (D) an activator (hereinafter, also referred to as "component (D)" or "(D)") that can react with the transition metal compound having the cyclic η-bonding anionic ligand to form a complex that displays catalytic activity, but is not specifically limited to being prepared in this manner.

Examples of the inorganic support material (A) include, but are not specifically limited to, oxides such as $SiO_2$, $Al_2O_3$, MgO, and $TiO_2$; halogen compounds such as $MgCl_2$; and organically-modified clays obtained through modification with an aliphatic salt such as described in JP 2016-176061 A. Of these materials, $SiO_2$ is preferable as the support material.

Although no specific limitations are placed on the average particle diameter D50 of the inorganic support material, the average particle diameter D50 is preferably 1 μm to 50 μm since this enables excellent efficiency in catalyst preparation and excellent efficiency in polyethylene production. In order to set the span of the polyethylene polymer powder within any of the ranges set forth above, it is preferable that a precursor of the inorganic support material having an average particle diameter of 1 μm to 100 μm is pulverized using a pulverizer such as a jet mill.

The inorganic support material (A) is preferably treated with an organoaluminum compound (B) as necessary. Preferable examples of the organoaluminum compound (B) include, but are not specifically limited to, alkylaluminums such as trimethylaluminum, triethylaluminum, triisobutylaluminum, trihexylaluminum, and trioctylaluminum; alkylaluminum hydrides such as diethylaluminum hydride and diisobutylaluminum hydride; aluminum alkoxides such as diethylaluminum ethoxide and dimethylaluminum methoxide; and alumoxanes such as methylalumoxane, isobutylalumoxane, and methylisobutylalumoxane. Of these organoaluminum compounds, trialkylaluminums and aluminum alkoxides are preferable, and trimethylaluminum, triethylaluminum, and triisobutylaluminum are more preferable.

The supported metallocene catalyst may include a transition metal compound (C) having a cyclic η-bonding anionic ligand (hereinafter, also referred to simply as the "transition metal compound"). The transition metal compound according to the present embodiment may be represented by the following formula (1), for example, but is not specifically limited thereto.

In formula (1), M represents a transition metal from group 4 of the periodic table that has an oxidation number of +2, +3, or +4 and is $\eta^5$-bonded to one or more ligands L.

Each L in formula (1) independently represents a cyclic η-bonding anionic ligand. The cyclic η-bonding anionic ligand is a cyclopentadienyl group, an indenyl group, a tetrahydroindenyl group, a fluorenyl group, a tetrahydrofluorenyl group, or an octahydrofluorenyl group, where these groups may optionally have 1 to 8 substituents selected independently from a hydrocarbon group, a halogen, a halogen-substituted hydrocarbon group, an aminohydrocarbyl group, a hydrocarbyloxy group, a dihydrocarbylamino group, a hydrocarbylphosphino group, a silyl group, an aminosilyl group, a hydrocarbyloxysilyl group, and a halosilyl group that contain up to 20 non-hydrogen atoms, and two ligands L may be bonded through a divalent substituent such as a hydrocarbadiyl, a halohydrocarbadiyl, a hydrocarbyleneoxy, a hydrocarbyleneamino, a siladiyl, a halosiladiyl, or an aminosilane that contains up to 20 non-hydrogen atoms.

Each X in formula (1) independently represents a monovalent anionic σ-bonding ligand, a divalent anionic σ-bonding ligand that bonds divalently to M, or a divalent anionic σ-bonding ligand that bonds monovalently to both M and L, said X containing up to 60 non-hydrogen atoms. Each X' independently represents a neutral Lewis base coordinating compound selected from phosphines, ethers, amines, olefins, and conjugated dienes and having a carbon number of 4 to 40.

In formula (1), l represents an integer of 1 or 2. Moreover, p represents an integer of 0, 1, or 2. In a case in which X represents a monovalent anionic σ-bonding ligand or a divalent anionic σ-bonding ligand that is bonded monovalently to each of M and L, p represents an integer that is at least 1 less than the formal oxidation number of M, and in a case in which X represents a divalent anionic σ-bonding ligand that is divalently bonded to M, p represents an integer that is at least 1+1 less than the formal oxidation number of M. Furthermore, q represents an integer of 0, 1, or 2. The transition metal compound is preferably a transition metal compound for which 1 in formula (1) represents 1.

Suitable examples of the transition metal compound include compounds represented by the following formula (2).

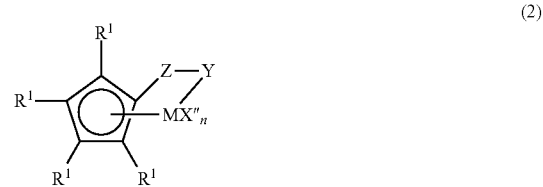

M in formula (2) represents titanium, zirconium, or hafnium having a formal oxidation number of +2, +3, or +4. Each $R^1$ in formula (2) independently represents hydrogen, a hydrocarbon group, a silyl group, a germyl group, a cyano group, a halogen, or a composite group of any thereof, each of which may contain up to 20 non-hydrogen atoms. Moreover, adjacent $R^1$ groups may combine to form a divalent derivative such as a hydrocarbadiyl, a siladiyl, or a germadiyl in a cyclic structure.

Each X" in formula (2) independently represents a halogen, a hydrocarbon group, a hydrocarbyloxy group, a hydrocarbylamino group, or a silyl group, each of which may contain up to 20 non-hydrogen atoms. Moreover, two X" groups may form a neutral conjugated diene having a carbon number of 5 to 30 or a divalent derivative. Y represents —O—, —S—, —NR³—, or —PR³—, Z represents $SiR^3{}_2$, $CR^3{}_2$, $SiR^3{}_2SiR^3{}_2$, $CR^3{}_2CR^3{}_2$, $CR^3=CR^3$, $CR^3{}_2SiR^3{}_2$, or $GeR^3{}_2$, and each $R^3$ independently represents an alkyl group having a carbon number of 1 to 12 or an allyl group. Moreover, n represents an integer of 1 to 3.

More suitable examples of the transition metal compound include compounds represented by the following formulae (3) and (4).

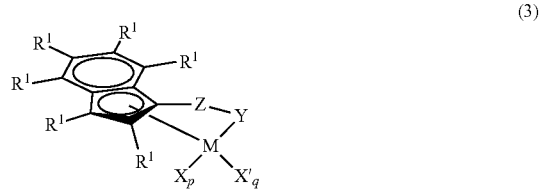

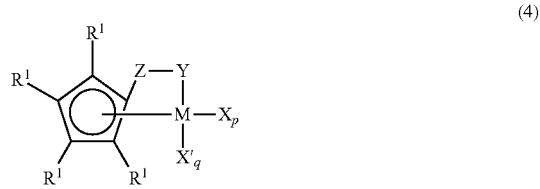

Each $R^1$ in formulae (3) and (4) independently represents hydrogen, a hydrocarbon group, a silyl group, a germyl group, a cyano group, a halogen, or a composite group of any thereof, and may contain up to 20 non-hydrogen atoms. M represents titanium, zirconium, or hafnium. Z and Y represent the same as in formula (2). Moreover, X and X' represent the same as X" in formula (2).

In each of formulae (3) and (4), p represents 0, 1, or 2, and q represents 0 or 1. In a case in which p is 2 and q is 0, M has an oxidation number of +4 and X represents a halogen, a hydrocarbon group, a hydrocarbyloxy group, a dihydrocarbylamide group, a dihydrocarbylphosphide group, a hydrocarbylsulfide group, a silyl group, or a composite group of any thereof, and may contain up to 20 non-hydrogen atoms.

In each of formulae (3) and (4), in a case in which p is 1 and q is 0, M has an oxidation number of +3 and X represents a stabilizing anionic ligand selected from an allyl group, a 2-(N,N-dimethylaminomethyl)phenyl group, and a 2-(N,N-dimethyl)-aminobenzyl group; or M has an oxidation number of +4 and X represents a derivative of a divalent conjugated diene; or M and X form a metallocyclopentene group together.

In each of formulae (3) and (4), in a case in which p is 0 and q is 1, M has an oxidation number of +2 and X' is a neutral conjugated or non-conjugated diene that is optionally substituted with one or more hydrocarbon groups. Moreover, X' may contain up to 40 carbon atoms and forms a π-type complex with M.

Even more suitable examples of the transition metal compound include compounds represented by the following formulae (5) and (6).

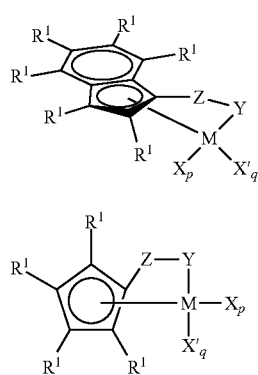

(5)

(6)

In each of formulae (5) and (6), each $R^1$ independently represents hydrogen or an alkyl group having a carbon number of 1 to 6. Moreover, M represents titanium and Y represents —O—, —S—, —$NR^3$—, or —$PR^3$—. Z represents $SiR^3{}_2$, $CR^3{}_2$, $SiR^3{}_2SiR^3{}_2$, $CR^3{}_2CR^3{}_2$, $CR^3$=$CR^3$, $CR^3{}_2SiR^3{}_2$, or $GeR^3{}_2$, and each $R^3$ independently represents hydrogen, a hydrocarbon group, a hydrocarbyloxy group, a silyl group, a halogenated alkyl group, a halogenated allyl group, or a composite group of any thereof, which may each contain up to 20 non-hydrogen atoms. Moreover, two $R^3$ groups in Z or an $R^3$ group in Z and an $R^3$ group in Y may form a cyclic structure in combination as necessary. X and X' represent the same as in formula (3) or (4).

In each of formulae (5) and (6), p represents 0, 1, or 2, and q represents 0 or 1. However, in a case in which p is 2 and q is 0, M has an oxidation number of +4 and each X independently represents a methyl group or a benzyl group. Moreover, in a case in which p is 1 and q is 0, M has an oxidation number of +3 and X represents 2-(N,N-dimethyl) aminobenzyl; or M has an oxidation number of +4 and X represents 2-buten-1,4-diyl. Furthermore, in a case in which p is 0 and q is 1, M has an oxidation number of +2 and X' represents 1,4-diphenyl-1,3-butadiene or 1,3-pentadiene. These dienes exemplify asymmetric dienes forming a metal complex and are actually mixtures of geometric isomers.

The supported metallocene catalyst includes an activator (D) that can react with the transition metal compound to form a complex that displays catalytic activity (hereinafter, also referred to simply as an "activator"). In a metallocene catalyst, a complex formed by a transition metal compound and the aforementioned activator normally displays high olefin polymerization activity as a catalytically active species. Examples of the activator in the present embodiment include, but are not specifically limited to, compounds represented by the following formula (7).

(7)

In formula (7), $[L-H]^{d+}$ represents a proton donating Bronsted acid and L represents a neutral Lewis base. Moreover, $[M_mQ_p]^{d-}$ represents a compatible non-coordinating anion, M represents a metal or metalloid selected from groups 5 to 15 of the periodic table, and each Q independently represents a hydride, a dialkylamide group, a halide, an alkoxy group, an allyloxy group, a hydrocarbon group, or a substituted hydrocarbon group having a carbon number of up to 20, but not more than one Q is a halide. Furthermore, m represents an integer of 1 to 7, p represents an integer of 2 to 14, d represents an integer of 1 to 7, and p−m=d.

More preferable examples of the activator include compounds represented by the following formula (8).

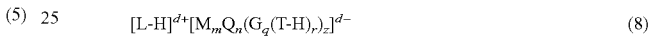

(8)

In formula (8), $[L-H]^{d+}$ represents a proton donating Bronsted acid and L represents a neutral Lewis base. Moreover, $[M_mQ_n(G_q(T-H)_r)_z]^{d-}$ represents a compatible non-coordinating anion, M represents a metal or metalloid selected from groups 5 to 15 of the periodic table, and each Q independently represents a hydride, a dialkylamide group, a halide, an alkoxy group, an allyloxy group, a hydrocarbon group, or a substituted hydrocarbon group having a carbon number of up to 20, but not more than one Q is a halide. Furthermore, G represents a polyvalent hydrocarbon group having a valence of r+1 that bonds to M and T, and T represents O, S, NR, or PR. R represents a hydrocarbyl, a trihydrocarbylsilyl group, a trihydrocarbylgermanium group, or hydrogen. Moreover, m represents an integer of 1 to 7, n represents an integer of 0 to 7, q represents an integer of 0 or 1, r represents an integer of 1 to 3, z represents an integer of 1 to 8, d represents an integer of 1 to 7, and n+z−m=d.

Even more preferable examples of the activator include compounds represented by the following formula (9).

(9)

In formula (9), $[L-H]^+$ represents a proton donating Bronsted acid and L represents a neutral Lewis base. Moreover, $[BQ_3Q^1]^-$ represents a compatible non-coordinating anion, B represents boron, each Q independently represents a pentafluorophenyl group, and $Q^1$ represents a substituted aryl group having one OH group as a substituent and having a carbon number of 6 to 20.

Examples of the proton donating Bronsted acid include, but are not specifically limited to, trialkyl group-substituted ammonium cations such as tri ethyl ammonium, tripropylammonium, tri(n-butyl)ammonium, trimethylammonium, tributylammonium, tri(n-octyl)ammonium, diethylmethylammonium, dibutylmethylammonium, dibutylethylammonium, dihexylmethylammonium, dioctylmethylammonium, didecylmethylammonium, didodecylmethylammonium, ditetradecylmethylammonium, dihexadecylmethylammonium, dioctadecylmethylammonium, diicosylmethylammonium, and bis(hydrogenated tallow alkyl)methylammonium; N,N-dialkylanilinium cations such as N,N-dimethylanilinium, N,N-diethylanilinium, N,N-2,4,6-pentamethylanilinium, and N,N-dimethylbenzylanilinium; and a triphenylcarbonium cation.

Examples of the compatible non-coordinating anion include, but are not specifically limited to, triphenyl(hydroxyphenyl)borate, diphenyl-di(hydroxyphenyl)borate, triphenyl(2,4-dihydroxyphenyl)borate, tri(p-tolyl)(hydroxyphenyl)borate, tris(pentafluorophenyl)(hydroxyphenyl)borate, tris(2,4-dimethylphenyl)(hydroxyphenyl)borate, tris (3,5-dimethylphenyl)(hydroxyphenyl)borate, tris(3,5-ditrifluoromethylphenyl)(hydroxyphenyl)borate, tris (pentafluorophenyl)(2-hydroxyethyl)borate, tris (pentafluorophenyl)(4-hydroxybutyl)borate, tris (pentafluorophenyl)(4-hydroxy-cyclohexyl)borate, tris (pentafluorophenyl)(4-(4'-hydroxyphenyl)phenyl)borate, and tris(pentafluorophenyl)(6-hydroxy-2-naphthyl)borate. These compatible non-coordinating anions may also be referred to as "borate compounds". The activator of the supported metallocene catalyst is preferably a borate compound from a viewpoint of catalytic activity and from a viewpoint of reducing the total content of Al, Mg, Ti, Zr, and Hf. Examples of preferable borate compounds include tris (pentafluorophenyl)(hydroxyphenyl)borate.

It is also possible to use an organometallic oxy compound having a unit represented by the following formula (10) as the activator. However, in such a case, the Al content of the polyethylene polymer powder tends to increase.

$$\pm M^2R_{n-2}-O\pm_m \qquad (10)$$

(In formula (10), $M^2$ represents a metal or metalloid from groups 13 to 15 of the periodic table, each R independently represents a hydrocarbon group or a substituted hydrocarbon group having a carbon number of 1 to 12, n represents the valence of the metal $M^2$, and m represents an integer of 2 or more.)

Another preferable example of the activator is an organoaluminum oxy compound containing a unit represented by the following formula (11).

$$\pm AlR-O\pm_m \qquad (11)$$

(In formula (11), R represents an alkyl group having a carbon number of 1 to 8 and m represents an integer of 2 to 60.)

A more preferable example of the activator is methylalumoxane containing a unit represented by the following formula (12).

$$\pm Al(CH_3)-O\pm_m \qquad (12)$$

(In formula (12), m represents an integer of 2 to 60.)

Besides the components (A) to (D) described above, an organoaluminum compound may be used as a catalyst as necessary. Examples of the organoaluminum compound include, but are not specifically limited to, compounds represented by the following formula (13).

$$AlR_nX_{3-n} \qquad (13)$$

In formula (13), R represents a linear, branched, or cyclic alkyl group having a carbon number of 1 to 12 or an aryl group having a carbon number of 6 to 20, X represents a halogen, hydrogen, or an alkoxyl group, and n represents an integer of 1 to 3. Moreover, the organoaluminum compound may be a mixture of compounds represented by formula (13).

The catalyst can be obtained by supporting component (B), component (C), and component (D) on component (A). Examples of methods by which component (B), component (C), and component (D) can be supported include, but are not specifically limited to, a method in which component (B), component (C), and component (D) are dissolved in an inert solvent in which each of these components is soluble, are mixed with component (A), and then the solvent is evaporated; a method in which component (B), component (C), and component (D) are dissolved in an inert solvent, concentrating thereof is subsequently performed within a range for which precipitation of solid does not occur, and then component (A) is added in an amount that can retain all of the concentrated liquid in particles thereof; a method in which component (B) and component (D) are first supported on component (A), and then component (C) is supported; and a method in which components (B) and (D) and component (C) are successively supported on component (A). In the present embodiment, component (C) and component (D) are preferably liquids or solids. Moreover, there are cases in which component (B), component (C), and component (D) are diluted in an inert solvent before being used in the supporting.

Examples of the inert solvent include, but are not specifically limited to, aliphatic hydrocarbons such as hexane, heptane, octane, decane, dodecane, and kerosene; alicyclic hydrocarbons such as cyclohexane and methylcyclopentane; aromatic hydrocarbons such as benzene, toluene, and xylene; and mixtures of any of the preceding examples. The inert solvent is preferably used after impurities such as water, oxygen, and sulfur content have been removed using a drying agent, an adsorbent, or the like.

The amount of component (B) that is supported in terms of Al atoms relative to 1.0 g of component (A) is preferably at least 0.5 mmol and not more than 5.0 mmol, and more preferably at least 1.0 mmol and not more than 2.5 mmol, and the amount of component (C) and component (D) that is supported relative to 1.0 g of component (A) is preferably at least 50 µmol and not more than 200 µmol, and more preferably at least 80 µmol and not more than 180 µm. The amount and method of support of each component may be selected based on activity, cost, powder characteristics, reactor internal scale, and so forth. The resultant supported metallocene catalyst may be washed by decantation, filtration, or the like using an inert solvent with the aim of removing organoaluminum compound, borate compound, and titanium compound that are not supported on the support.

The series of operations of dissolving, contacting, washing, and so forth described above is preferably performed with a temperature of at least −30° C. and not higher than 80° C. selected for each unit operation. A more preferable temperature range is at least 0° C. and not higher than 50° C. In particular, the temperature during supporting of component (C) and component (D) is preferably at least 0° C. and not higher than 20° C., and more preferably at least 5° C. and not higher than 15° C. Setting the supporting conditions of components (C) and (D) within any of the ranges set forth above tends to result in a heat of fusion ΔH1 that is within the previously described range. Moreover, the series of operations by which the supported metallocene catalyst is obtained is preferably carried out in a dry and inert atmosphere.

Although the supported metallocene catalyst enables homopolymerization of ethylene or copolymerization of ethylene and an α-olefin by itself, an organoaluminum compound may be provided in conjunction therewith as an additional component in order to prevent solvent or reaction poisoning. Preferable examples of the organoaluminum compound include, but are not specifically limited to, alkylaluminums such as trimethylaluminum, triethylaluminum, triisobutylaluminum, trihexylaluminum, and trioctylaluminum; alkylaluminum hydrides such as diethylaluminum hydride and diisobutylaluminum hydride; aluminum alkoxides such as diethylaluminum ethoxide; and alumoxanes such as methylalumoxane, isobutylalumoxane, and methylisobutylalumoxane. Of these organoaluminum compounds, trialkylaluminums and aluminum alkoxides are preferable, and triisobutylaluminum is more preferable.

The polymerization method of the polyethylene polymer powder is preferably slurry polymerization. In general, the polymerization pressure when carrying out polymerization is preferably at least 0.1 MPaG and not higher than 10 MPaG, and more preferably at least 0.3 MPaG and not higher than 3.0 MPaG. Moreover, the polymerization temperature is preferably at least 20° C. and not higher than 115° C., and more preferably at least 50° C. and not higher than 85° C.

The solvent used in slurry polymerization may suitably be any of the previously described inert solvents and is more preferably an inert hydrocarbon solvent. The inert hydrocarbon solvent may be a hydrocarbon solvent having a carbon number of at least 6 and not more than 8. Specific examples include aliphatic hydrocarbons such as hexane, heptane, and octane; alicyclic hydrocarbons such as cyclohexane and methylcyclopentane; and mixtures of any of the preceding examples.

In the polymerization method of the polyethylene polymer powder, polymerization is preferably carried out in a continuous manner. By continuously supplying ethylene gas, a solvent, a catalyst, and so forth in polymerization system and continuously discharging these materials with produced polyethylene polymer powder, it is possible to inhibit a localized high-temperature state arising due to rapid reaction of ethylene, and the polymerization system tends to be more stable.

In the present embodiment, it is preferable that a loop reactor is used in slurry polymerization. Moreover, in a case in which a loop reactor is used in the present embodiment to produce the polyethylene polymer powder through slurry polymerization of ethylene as a raw material or through slurry polymerization of ethylene and an α-olefin as raw materials, it is more preferable that supply of the solvent and raw materials in polymerization is performed by a plurality of supply lines. Specifically, when a solvent, such as hexane, and a raw material (ethylene or ethylene and an α-olefin) are taken to be one group of supply lines, it is preferable that the solvent and the raw material are supplied into the polymerization system by a plurality of groups of supply lines in polymerization. In other words, it is preferable to adopt a method in which feeding inlets for the raw material and the solvent are split into two or more locations each. By adopting this method, it is possible to effectively set both the span, which is an indicator of particle size distribution, and the melting peak full width at half maximum, which is an indicator of ease of melting, within the previously described ranges.

The method by which the solvent is separated in the method of producing a polyethylene polymer powder according to the present embodiment may be decantation, centrifugation, filtration, or the like, and is more preferably centrifugation because this enables good separation efficiency of the polyethylene polymer powder and the solvent. Although no specific limitations are placed on the amount of the solvent that is contained in the polyethylene polymer powder after solvent separation, the amount of the solvent relative to the mass of the polyethylene polymer powder is preferably at least 50 mass % and not more than 90 mass %, more preferably at least 55 mass % and not more than 85 mass %, and even more preferably at least 60 mass % and not more than 80 mass %.

The method by which the catalyst used in synthesis of the polyethylene polymer powder is deactivated is preferably a method in which deactivation is implemented after separation of the polyethylene polymer powder and the solvent, but is not specifically limited thereto.

Examples of chemical agents that can be used to deactivate the catalyst include, but are not specifically limited to, oxygen, water, and alcohols.

Drying performed in the method of producing a polyethylene polymer powder is preferably carried out in a state of ventilation with an inert gas such as nitrogen or argon. The drying temperature is preferably at least 25° C. and not higher than 100° C., more preferably at least 30° C. and not higher than 90° C., and even more preferably at least 35° C. and not higher than 85° C. A drying temperature within any of the ranges set forth above tends to lower the heat of fusion $\Delta H1$.

EXAMPLES

The following provides a more detailed description of the present embodiment based on examples. However, the present embodiment is not limited to the following examples. First, measurement methods and evaluation criteria for physical properties and evaluations are explained below.

Physical Property 1: Intrinsic Viscosity (IV)

The intrinsic viscosity (IV) of each polyethylene polymer powder obtained in the subsequently described examples and comparative examples was determined in accordance with ISO 1628-3 (2010) by the following method.

First, the polyethylene polymer powder was weighed into a dissolving tube in a range of 4.0 mg to 4.5 mg (mass denoted as "m" in the following equation) and a vacuum pump was used to perform degassing and nitrogen substitution of air inside the dissolving tube. Thereafter, 20 mL of decahydronaphthalene (product having 1 g/L of 2,6-di-t-butyl-4-methylphenol added thereto; hereinafter, referred to as decalin) that had been subjected to degassing and nitrogen substitution using a vacuum pump was added, and stirring was performed for 90 minutes at 150° C. to dissolve the polyethylene polymer powder and yield a decalin solution. The decalin solution was subsequently charged to a Cannon-Fenske viscometer (produced by Sibata Scientific Technology Ltd.; product number: 100) in a 135° C. thermostatic bath, and the time of fall (ts) between reference lines was measured. The time of fall (tb) of decalin without adding the polyethylene polymer powder was measured as a blank. The specific viscosity ($\eta sp$) was determined by the following equation A.

$$\eta sp = ts/tb - 1 \qquad \text{(Equation A)}$$

The intrinsic viscosity IV was calculated from the specific viscosity ($\eta sp$) and the concentration (C) (units: g/dL) using the followings equations B and C.

$$C = m/(20 \times \gamma)/10 \text{ (units: g/dL)} \qquad \text{(Equation B)}$$
$$\gamma = \text{(Density of decalin at 20° C.)}/$$
$$\text{(Density of decalin at 135° C.)} =$$
$$0.888/0.802 = 1.107$$

$$IV = (\eta sp/C)/(1 + 0.27 \times \eta sp) \qquad \text{(Equation C)}$$

Physical property 2: Melting peak temperature (Tm1), heat of fusion (ΔH1), melting peak full width at half maximum (Tw), and 5% melting temperature (T5%)

The melting peak temperature (Tm1), the heat of fusion (ΔH1), the melting peak full width at half maximum (Tw), and the 5% melting temperature (T5%) of each polyethylene polymer powder obtained in the examples and comparative examples were measured using a DSC8000 produced by PerkinElmer Inc. as a differential scanning calorimeter (DSC). The polyethylene polymer powder was weighed out in an amount of 8.3 mg to 8.5 mg and was loaded into an aluminum sample pan. An aluminum cover was attached to the pan and the pan was set in the differential scanning calorimeter. Purging with nitrogen at a flow rate of 20 mL/min was performed while holding the sample and a reference sample for 1 minute at 50° C. and then heating the sample and the reference sample to 180° C. at a rate of 10° C./min. The temperature at the peak top of a melting curve obtained during this heating was taken to be the melting peak temperature (Tm1) and the temperature width at half the height of the melting peak height was taken to be the melting peak full width at half maximum (Tw). Moreover, the heat of fusion (ΔH1) was determined by dividing the total heat calculated from the melting peak area by the sample weight, and a temperature at which 5% of the total heat was reached was taken to be the 5% melting temperature (T5%).

Physical Property 3: D50 and Span

The D50 and span of each polyethylene polymer powder obtained in the examples and comparative examples were determined by the following method. A laser particle size distribution analyzer (product name: SALD-2100) produced by Shimadzu Corporation was used to measure the polyethylene polymer powder with methanol as a dispersion medium to prepare a cumulative particle size distribution from a small diameter end of the distribution. Particle diameters corresponding to cumulative values of 10%, 50%, and 90% were taken to be the D10, D50, and D90, respectively. The span was subsequently calculated as an indicator expressing the breadth of the particle size distribution using the following equation D.

$$\text{Span}=(D90-D10)/D50 \quad \text{(Equation D)}$$

Physical Property 4: α-Olefin Content

The α-olefin content of each polyethylene polymer powder obtained in the examples and comparative examples was measured by $^{13}$C-NMR under the following conditions.

Device: AVANCEIII 500HD Prodigy (Bruker Bio Spin)
Observation frequency: 125.77 MHz ($^{13}$C)
Pulse width: 5.0 μsec
Pulse repetition time: 5 sec
Number of integrations: 10,000
Measurement temperature: 120° C.
Reference: 29.9 ppm (PE: Sδδ)
Solvent: o-$C_6D_4Cl_2$
Sample concentration: 0.1 g/mL
Sample tube: 5 mm in diameter The measurement sample was obtained by adding 0.6 mL of o-$C_6D_4Cl_2$ to 60 mg of the polyethylene polymer powder and dissolving the polyethylene polymer powder under heating at 130° C.

The α-olefin content was determined from the spectrum obtained through measurement after attributing the observed peaks in accordance with (1) "J. Polym. Sci. Part A: Polym. Chem., 29, 1987-1990 (1991)" with regards to an ethylene-propylene copolymer, (2) "Macromolecules, 15, 353-360 (1982)" with regards to an ethylene-1-butene copolymer, and (3) "Macromolecules, 15, 1402-1406 (1982)" with regards to an ethylene-1-hexene copolymer.

Evaluations 1 and 2: Molding and Tensile Break Strength Measurement of Molded Product Production of a molded product in examples according to the present disclosure and comparative examples was performed by the following method. The polyethylene polymer powder was loaded into a mold having a thickness of 3 mm, was subjected to preliminary pressing for 4 minutes at a specific temperature and a pressure of 0.1 MPa, and was then subjected to melt-pressing for 6 minutes at 20 MPa. The molding temperature was set as 190° C. (molding condition 1 in Table 1) or 210° C. (molding condition 2 in Table 1).

Note that in Comparative Examples 2, 4, and 5, it was not possible to obtain a homogeneous molded product in the case of a molding condition of 190° C.

A sample was cut out from the molded product in dumbbell form (width of measured portion: 5 mm) and was left for 48 hours at a temperature of 23° C. and a humidity of 45%. Thereafter, a tensile test was carried out with a measurement temperature of 23° C., an initial specimen length of 20 mm, and a tensing rate of 20 mm/min using a tensile tester (produced by A&D Company, Limited; product name: TENSILON RTG-1210) to determine the tensile break strength.

Evaluation 3: Evaluation of Wear Resistance of Molded Product

The polyethylene polymer powder was loaded into a mold having a thickness of 10 mm and was subjected to press molding for 20 minutes at a mold temperature of 190° C. and a surface pressure of 30 MPa to obtain a molded product of 150 mm in length, 150 mm in width, and 10 mm in thickness.

The molded product was machined by a planing machine to prepare a circular rod of 5 mm in diameter and 8 mm in height as a sample for evaluation of wear resistance. A friction and wear tester (produced by Orientec Co., Ltd.; model: EFM-III-EN) was used to measure the amount of wear in accordance with JIS K7218 under conditions of a speed of 2.0 m/sec, a load of 25 MPa, a time of 360 minutes, and an opposing material of SS400.

The amount of wear was evaluated by the following index.

Good: Amount of wear of less than 15 mg
Satisfactory: Amount of wear of at least 15 mg and less than 30 mg
Poor: Amount of wear of 30 mg or more Evaluation 4: Evaluation of Surface Smoothness of Molded Product The molded product of 3 mm in thickness that was produced at 190° C. in Evaluation 1 was evaluated in terms of surface roughness. The number of particle-shaped lumps of 50 μm or larger (presumed to be inadequately melted powder) that were present in an area of 250 mm×250 mm was counted visually. The surface smoothness was evaluated by the following criteria based on the obtained number.

Good: 10 or fewer particle-shaped lumps
Satisfactory: 11 to 20 particle-shaped lumps
Poor: 21 or more particle-shaped lumps Evaluation 5: γ-Ray Crosslinking and Crosslinking Density A ram extruder (horizontal ram extruder with a ram length of approximately 1.2 m under a pressure of approximately 12 MPa and with temperature settings of a cylinder internal temperature of approximately 240° C. and a molding die temperature of approximately 200° C.) was used to shape the polyethylene polymer powder to obtain a molded product in the form of a circular rod. A rod of 90 mm in diameter and 500 mm in length was cut out from this molded product. A γ-ray treatment device having a cobalt-60 radiation source was used to subject the rod to γ-ray irradiation at an irradiation rate of 15.0 kGy per 1 hour until a total dose of 35 kGy was reached while the rod was exposed to the atmosphere. After this γ-ray irradiation, thermal annealing treatment was performed for 12 hours at 110° C. The crosslinking density was measured in accordance with a procedure reported by F. W. Shen et al. and was evaluated by the following index (refer to "Journal of Polymer Science, Part B: Polymer Physics, Vol. 34, 1996").

Good: Crosslinking density of 1.3 mol % or more
Satisfactory: Crosslinking density of at least 0.8 mol % and less than 1.3 mol %
Poor: Crosslinking density of less than 0.8 mol %

Evaluation 6: Evaluation of Wear Resistance of γ-Ray-Crosslinked Molded Product

The γ-ray-crosslinked molded product that was obtained in Evaluation 5 was subjected to a rotation wear test in which a high-purity alumina ball of ⅜ inch in diameter that had been subjected to mirror surface processing was pressed against the molded product under a pressure of 10 N for 24 hours at a rotation speed of 180 rpm and in physiological saline. The test was performed using a viscoelastic rheometer AR2000 produced by Seiko Instruments Inc. The cross-sectional area and depth of a worn portion was measured through three-dimensional measurement of deformation/wear of the specimen subjected to the test. The amount of volume reduction was calculated, and wear resistance was evaluated by the following index. Note that although evaluation of wear resistance is normally performed after removing a 1 mm surface layer in order to avoid the influence of initial wear due to surface degradation resulting from γ-ray processing, measurement was performed without surface layer removal in the present evaluation.

Good: Amount of wear of less than 2,000 $mm^3$
Satisfactory: Amount of wear of at least 2,000 $mm^3$ and less than 16,000 $mm^3$
Poor: Amount of wear of 16,000 $mm^3$ or more

[Preparation of Catalyst]

(Preparation of Supported Metallocene Catalyst [A])

H-201 silica (average particle diameter: 20 μm; pore volume: 1 mL/g; specific surface area: 700 $m^2$/g) produced by AGC Si-Tech Co., Ltd. was pulverized to an average particle diameter of 8 μm using a single track jet mill (produced by Seishin Enterprise Co., Ltd.; product name: CO-JET SYSTEM α MARK IV). Thereafter, 40 g of pulverized silica that had been baked at 550° C. in a nitrogen atmosphere was charged to an autoclave having a capacity of 1.8 L in 800 mL of hexane, was maintained at 25° C. under stirring, and 68 mL of a hexane solution of triethylaluminum (concentration: 1 mol/L) was added thereto. Stirring was subsequently performed for 2 hours to cause the triethylaluminum to react with surface silanol groups of the silica to obtain a hexane slurry of a component [a] having surface silanol groups of the silica capped with triethylaluminum.

Moreover, a component [b] was obtained by dissolving 200 mmol of [(N-t-butylamido)(tetramethyl-$\eta^5$-cyclopentadienyl)dimethyl silane]titanium dimethyl (hereinafter, referred to as the "titanium complex") in 1,000 mL of ISOPAR E® (ISOPAR E is a registered trademark in Japan, other countries, or both; product name of hydrocarbon mixture produced by Exxon Mobil Corporation (United States of America)), adding 20 mL of a 1 mol/L hexane solution of n-butylethylmagnesium, and further adding hexane to adjust the titanium complex concentration to 100 mmol/L.

Additionally, 5.7 g of bis(hydrogenated tallow alkyl) methylammonium-tris(pentafluorophenyl)(4-hydroxyphenyl)borate (hereinafter, referred to as the "borate compound") was added to and dissolved in 50 mL of toluene to obtain a 100 mmol/L toluene solution of the borate compound. Next, 5 mL of a 1 mol/L hexane solution of diethylaluminum ethoxide was added to the toluene solution of the borate compound at room temperature, and further hexane was added to adjust the borate compound concentration in the solution to 70 mmol/L. Thereafter, stirring was performed for 1 hour at room temperature to obtain a reaction mixture containing the borate compound.

Simultaneous addition of 114 mL of the reaction mixture containing the borate compound and 80 mL of component [b] obtained as described above was performed with respect to 800 mL of the slurry of component [a] obtained as described above at 25° C. to 30° C., and stirring was performed for 3 hours to cause reaction and precipitation of the titanium complex and the borate, and physical adsorption onto the silica. Thereafter, a supernatant containing unreacted borate compound and titanium complex in the resultant reaction mixture was removed by decantation to obtain a supported metallocene catalyst [A] (denoted simply as "A" in Table 1) in which a catalytically active species was formed on the silica.

(Supported Metallocene Catalyst [B])

A supported metallocene catalyst [B] (denoted simply as "B" in Table 1) was obtained in accordance with preparation of the supported metallocene catalyst [A] with the exception that 40 g of silica for catalyst support that had been baked at 550° C. in a nitrogen atmosphere and that had an average particle diameter of 8 μm, a pore volume of 1.20 mL/g, and a specific surface area of 480 $m^2$/g was used as the silica for catalyst support.

(Supported Metallocene Catalyst [C])

A 1 L flask was charged with 300 mL of industrial alcohol (produced by Japan Alcohol Trading Co., Ltd.: product name: EKINEN F-3) and 300 mL of distilled water, and then 15.0 g of concentrated hydrochloric acid and 42.4 g (120 mmol) of dimethyl behenyl amine (produced by Lion Corporation; product name: ARMIN DM22D) were added into the flask. These materials were heated to 45° C. and 100 g of synthetic hectorite (produced by Rockwood Additives Ltd.; product name: LAPONITE RDS) was dispersed. Thereafter, the temperature was increased to 60° C. and stirring was performed for 1 hour while maintaining this temperature. The slurry was filtered, was subsequently washed twice with 600 mL of 60° C. water, and was dried for 12 hours in an 85° C. dryer to obtain 125 g of an organically-modified clay. The organically-modified clay was pulverized to a median diameter of 7 μm by a jet mill.

A 300 mL flask equipped with a thermometer and a reflux tube was purged with nitrogen and was then charged with 25.0 g of the organically-modified clay obtained as described above and 108 mL of hexane. Next, 0.600 g of diphenylmethylene(cyclopentadienyl)(2-(dimethylamino)-9-fluorenyl)zirconium dichloride and 142 mL of 20% triisobutylaluminum were added into the flask and stirring was performed for 3 hours at 60° C. After cooling had been performed to 45° C., the supernatant was removed and washing was performed twice with 200 mL of hexane to obtain a supported metallocene catalyst [C] (denoted simply as "C" in Table 1).

Example 1

A polyethylene polymer powder was obtained by continuous slurry polymerization described below. Specifically, a pipe loop polymerization reactor having an internal capacity of 290 L was used to perform continuous polymerization under conditions of a polymerization temperature of 75° C., a polymerization pressure of 0.80 MPaG, and an average residence time of 1.8 hours. Dehydrated normal hexane was supplied as a solvent at 80 L/hour, the supported metallocene catalyst [A] described above was supplied as a catalyst at 1.4 mmol/hour in terms of Ti atoms, and triisobutylaluminum was supplied at 20 mmol/hour. Copolymerization of ethylene and 1-butene was performed by supplying 84 ppm of hydrogen for molecular weight adjustment relative to the gas phase concentration of ethylene and 1-butene and supplying 0.15 mol % of 1-butene relative to the gas phase concentration of ethylene. The supply of raw materials was performed by splitting feeding inlets for the ethylene, the α-olefin, and the hexane into two locations each (i.e., two supply lines were used).

The polymerization slurry in the polymerization reactor was guided to a flash tank having a pressure of 0.05 MPa and a temperature of 70° C. such as to maintain the polymerization reactor at a constant level, and unreacted ethylene, 1-butene, and hydrogen were separated. Next, the slurry was continuously fed to a centrifugal separator such as to maintain the flash tank at a constant level, and powder was separated from solvent and the like other than the powder. The separated polyethylene polymer powder was transported to a rotary dryer and was dried under nitrogen blowing at a drying temperature of 75° C. with an average residence time of 60 minutes to obtain a polyethylene polymer powder of Example 1. Measurement results and evaluation results are shown in Table 1.

Examples 2 to 7 and Comparative Examples 1 and 2

Polyethylene polymer powders were obtained by the same method as in Example 1 with the exception that the catalyst, the polymerization temperature, the polymerization pressure, the hydrogen concentration, and the 1-butene concentration were set as shown in Table 1. Measurement results and evaluation results are shown in Table 1.

Comparative Examples 3 and 5

Polyethylene polymer powders were obtained by the same method as in Example 1 with the exception that a 340 L vessel-type polymerization reactor with a stirrer was used and the polymerization conditions were set as shown in Table 1. Measurement results and evaluation results are shown in Table 1.

Comparative Example 4

A polyethylene polymer powder was obtained by the same method as in Example 1 with the exception that a feeding inlet for the ethylene, α-olefin, and hexane used as raw materials was only provided at one location and the polymerization conditions were set as shown in Table 1. Measurement results and evaluation results are shown in Table 1.

Comparative Example 6

GUR1050 produced by Celanese Corporation was used as a polyethylene polymer powder. Evaluation results are shown in Table 1.

Comparative Example 7

A polyethylene polymer powder was obtained by the same method as in Example 1 with the exception that the average residence time was set as 0.6 hours and the polymerization conditions were set as shown in Table 1. Measurement results and evaluation results are shown in Table 1.

TABLE 1

|  |  | Units | Example 1 | Example 2 | Example 3 | Example 4 | Example 5 | Example 6 | Example 7 |
|---|---|---|---|---|---|---|---|---|---|
| Polymerization conditions | Reactor | — | Loop | Loop | Loop | Loop | Loop | Loop | Loop |
|  | Raw material feeding inlets | No. | 2 | 2 | 2 | 2 | 2 | 2 | 2 |
|  | Catalyst | — | A | A | A | A | A | A | A |
|  | Polymerization temperature | ° C. | 75 | 80 | 83 | 75 | 83 | 80 | 75 |
|  | Polymerization pressure | MPaG | 0.80 | 0.90 | 0.70 | 0.80 | 0.50 | 0.98 | 0.80 |
|  | Hydrogen concentration | ppm | 84 | 67 | 56 | 180 | 117 | 50 | 40 |
|  | Comonomer type | — | 1-Butene | 1-Butene | 1-Butene | 1-Butene | — | 1-Butene | 1-Butene |
|  | Comonomer concentration | mol % | 0.15 | 1.58 | 0.85 | 0.42 | 0 | 0.06 | 1.06 |
|  | Residence time | h | 1.80 | 1.80 | 1.80 | 1.80 | 1.80 | 1.80 | 1.80 |
| Physical property 1: Intrinsic viscosity (IV) | | dL/g | 19.5 | 23.1 | 26.9 | 17.0 | 16.0 | 31.1 | 35.0 |
| Physical property 2: Melting peak temperature Tml | | ° C. | 141 | 119 | 130 | 137 | 143 | 143 | 127 |
| Physical property 2: Melting peak full width at half maximum Tw | | ° C. | 6.6 | 6.1 | 5.7 | 4 | 4.7 | 6.0 | 7.0 |
| Physical property 2: Heat of fusion ΔHI | | J/g | 165 | 108 | 134 | 150 | 180 | 165 | 123 |
| Physical property 2: 5% Melting temperature T5% | | ° C. | 114 | 80 | 97 | 107 | 123 | 115 | 89 |
| Physical property 3: D50 | | μm | 167 | 100 | 268 | 223 | 180 | 138 | 70 |
| Physical property 3: Span | | — | 0.91 | 1.90 | 1.30 | 1.05 | 1.10 | 1.00 | 1.60 |
| Physical property 4: α-Olefin content | | mol % | 0.15 | 1.48 | 0.80 | 0.40 | 0.0 | 0.06 | 1.00 |
| Evaluation 1: Tensile break strength for molding condition 1 | | MPa | 54 | 45 | 40 | 45 | 55 | 63 | 68 |
| Evaluation 2: Tensile break strength for molding condition 2 | | MPa | 62 | 50 | 58 | 53 | 61 | 74 | 80 |
| Evaluation 3: Amount of wear | | Good/Satisfactory/Poor | Satisfactory | Good | Good | Satisfactory | Satisfactory | Good | Good |

TABLE 1-continued

| | Units Good/Satisfactory/Poor | | | | | | | |
|---|---|---|---|---|---|---|---|---|
| Evaluation 4: Unevenness of molded product surface | Good/Satisfactory/Poor | Good | Satisfactory | Good | Good | Satisfactory | Good | Satisfactory |
| Evaluation 5: γ-Ray crosslinking density | Good/Satisfactory/Poor | Good | Good | Good | Good | Satisfactory | Good | Satisfactory |
| Evaluation 6: Amount of wear after γ-ray crosslinking | Good/Satisfactory/Poor | Good | Satisfactory | Good | Good | Satisfactory | Good | Satisfactory |

| | | Units | Comparative Example 1 | Comparative Example 2 | Comparative Example 3 | Comparative Example 4 | Comparative Example 5 | Comparative Example 6 | Comparative Example 7 |
|---|---|---|---|---|---|---|---|---|---|
| Polymerization conditions | Reactor | — | Loop | Loop | Vessel | Loop | Vessel | — | Loop |
| | Raw material feeding inlets | No. | 2 | 2 | 2 | 1 | 2 | — | 2 |
| | Catalyst | — | A | B | B | A | C | — | A |
| | Polymerization temperature | °C. | 75 | 75 | 83 | 80 | 75 | — | 75 |
| | Polymerization pressure | MPaG | 0.80 | 0.80 | 0.50 | 0.98 | 0.80 | — | 0.81 |
| | Hydrogen concentration | ppm | 820 | 40 | 124 | 45 | 0 | — | 178 |
| | Comonomer type | — | 1-Butene | 1-Butene | — | 1-Butene | — | — | 1-Butene |
| | Comonomer concentration | mol % | 0.53 | 1.10 | 0 | 0.08 | 0 | — | 0.40 |
| | Residence time | h | 1.80 | 1.80 | 1.80 | 1.80 | 1.80 | — | 0.60 |
| Physical property 1: Intrinsic viscosity (IV) | | dL/g | 11.0 | 33.9 | 14.9 | 32.0 | 37.0 | 20.3 | 16.9 |
| Physical property 2: Melting peak temperature Tm1 | | °C. | 130 | 125 | 144 | 142 | 146.6 | 144 | 137 |
| Physical property 2: Melting peak full width at half maximum Tw | | °C. | 5.1 | 4.0 | 3.5 | 8.0 | 6.2 | 9.0 | 4.2 |
| Physical property 2: Heat of fusion ΔH1 | | J/g | 176 | 128 | 180 | 157 | 237 | 203 | 152 |
| Physical property 2: 5% Melting temperature T5% | | °C. | 95 | 86 | 120 | 113 | 124 | 106 | 109 |
| Physical property 3: D50 | | μm | 150 | 65 | 207 | 138 | 149 | 159 | 219 |
| Physical property 3: Span | | — | 0.90 | 0.70 | 0.6 | 1.15 | 0.80 | 0.75 | 0.87 |
| Physical property 4: α-Olefin content | | mol % | 0.50 | 1.12 | 0 | 0.06 | 0 | 0.04 | 0.38 |
| Evaluation 1: Tensile break strength for molding condition 1 | | MPa | 35 | — | 43 | — | — | 38 | 40 |
| Evaluation 2: Tensile break strength for molding condition 2 | | MPa | 36 | 70 | 42 | 63 | 65 | 30 | 50 |
| Evaluation 3: Amount of wear | | Good/Satisfactory/Poor | Poor | Good | Poor | Good | Good | Satisfactory | Poor |
| Evaluation 4: Unevenness of molded product surface | | Good/Satisfactory/Poor | Poor | Poor | Poor | Poor | Poor | Poor | Poor |
| Evaluation 5: γ-Ray crosslinking density | | Good/Satisfactory/Poor | Good | Satisfactory | Satisfactory | Good | Good | Poor | Satisfactory |
| Evaluation 6: Amount of wear after γ-ray crosslinking | | Good/Satisfactory/Poor | Poor | Poor | Poor | Poor | Poor | Poor | Poor |

It can be seen from Table 1 that molded products having high strength and excellent wear resistance were obtained in the examples even in cases in which molding efficiency was increased. Moreover, it can be seen that molded products in which polyethylene polymer powders obtained in the examples were used had high crosslinking density and low degradation after being subjected to γ-ray irradiation, which demonstrates that these molded products are suitable for prosthetic joint applications.

INDUSTRIAL APPLICABILITY

According to this disclosure, it is possible to provide a polyethylene polymer powder and method of producing the same that can improve molding efficiency while maintaining high levels of strength and wear resistance.

The invention claimed is:

1. A polyethylene polymer powder comprising an ethylene homopolymer or a copolymer of ethylene and an α-olefin having a carbon number of at least 3 and not more than 8, wherein the polyethylene polymer powder has an intrinsic viscosity IV of at least 12 dL/g and not more than 35 dL/g as measured at 135° C. in decalin solvent, the polyethylene polymer powder has a melting peak full width at half maximum of at least 2° C. and not more than 7° C. as measured by differential scanning calorimetry at a heating rate of 10° C./min, the polyethylene polymer powder has a span of at least 0.9 and not more than 2 as determined by laser particle size distribution measurement in methanol, and the polyethylene polymer powder has an α-olefin content of 0 mol % to not more than 1.50 mol % as measured by $^{13}$C-NMR.

2. The polyethylene polymer powder according to claim 1, wherein the polyethylene polymer powder has a heat of fusion ΔH1 of at least 100 J/g and not more than 200 J/g as measured by differential scanning calorimetry at a heating rate of 10° C./min, and a temperature at which 5% heat of fusion of the heat of fusion ΔH1 is reached is at least 90° C. and not higher than 120° C.

3. The polyethylene polymer powder according to claim 1 for a compression molded product.

4. The polyethylene polymer powder according to claim 1 for a prosthetic joint.

5. A prosthetic joint comprising a crosslinked molded product obtained through γ-ray irradiation of a molded product of the polyethylene polymer powder according to claim 1.

6. A method of producing the polyethylene polymer powder according to claim 1, comprising:
   polymerizing ethylene or ethylene and an α-olefin by slurry polymerization using a loop reactor, wherein
   in the polymerizing, supply of a solvent and ethylene or supply of a solvent, ethylene, and an α-olefin is performed by a plurality of supply lines.

7. The polyethylene polymer powder according to claim 2 for a compression molded product.

8. The polyethylene polymer powder according to claim 2 for a prosthetic joint.

9. A prosthetic joint comprising a crosslinked molded product obtained through γ-ray irradiation of a molded product of the polyethylene polymer powder according to claim 2.

10. A method of producing the polyethylene polymer powder according to claim 2, comprising:
    polymerizing ethylene or ethylene and an α-olefin by slurry polymerization using a loop reactor, wherein
    in the polymerizing, supply of a solvent and ethylene or supply of a solvent, ethylene, and an α-olefin is performed by a plurality of supply lines.

* * * * *